(12) United States Patent
Benson et al.

(10) Patent No.: US 11,426,274 B2
(45) Date of Patent: Aug. 30, 2022

(54) MULTI-LAYER STENT

(71) Applicant: St. Jude Medical, LLC, Abbott Park, IL (US)

(72) Inventors: Thomas M. Benson, Minneapolis, MN (US); Ott Khouengboua, Chaska, MN (US); Peter N. Braido, Wyoming, MN (US)

(73) Assignee: St. Jude Medical, LLC, Abbott Park, IL (US)

( * ) Notice: Subject to any disclaimer, the term of this patent is extended or adjusted under 35 U.S.C. 154(b) by 211 days.

(21) Appl. No.: 16/385,481

(22) Filed: Apr. 16, 2019

(65) Prior Publication Data

US 2019/0240009 A1  Aug. 8, 2019

Related U.S. Application Data

(63) Continuation of application No. 15/365,040, filed on Nov. 30, 2016, now abandoned, which is a
(Continued)

(51) Int. Cl.
  *A61F 2/24*  (2006.01)
  *A61F 2/82*  (2013.01)
  *A61F 2/90*  (2013.01)

(52) U.S. Cl.
  CPC .......... *A61F 2/2418* (2013.01); *A61F 2/2436* (2013.01); *A61F 2/82* (2013.01);
(Continued)

(58) Field of Classification Search
  CPC ...... A61F 2/2418; A61F 2/2436; A61F 2/844; A61F 2210/0076; A61F 2220/0058;
(Continued)

(56) References Cited

U.S. PATENT DOCUMENTS

| | | | |
|---|---|---|---|
| 7,331,993 B2 * | 2/2008 | White | A61F 2/2412 264/632 |
| 7,998,196 B2 | 8/2011 | Mathison | |

(Continued)

FOREIGN PATENT DOCUMENTS

| | | |
|---|---|---|
| WO | 03092554 A1 | 11/2003 |
| WO | 2006128193 A2 | 11/2006 |

(Continued)

OTHER PUBLICATIONS

International Search Report for Application No. PCT/US2012/042059 dated Jul. 29, 2013.

*Primary Examiner* — Paul B Prebilic
(74) *Attorney, Agent, or Firm* — Wei & Sleman LLP

(57) ABSTRACT

A collapsible prosthetic heart valve includes a stent and a valve assembly. The stent includes an annulus section and at least one foldable section. The stent is movable between an unfolded condition in which the foldable section is longitudinally spaced from the annulus section, and a folded condition in which the foldable section is at least partially positioned radially adjacent the annulus section. The valve assembly is positioned within the annulus section of the stent in the folded condition of the stent.

17 Claims, 7 Drawing Sheets

Related U.S. Application Data continuation of application No. 14/124,092, filed as application No. PCT/US2012/042059 on Jun. 12, 2012, now Pat. No. 9,532,887.

(60) Provisional application No. 61/497,291, filed on Jun. 15, 2011.

(52) U.S. Cl.
CPC ........ *A61F 2/90* (2013.01); *A61F 2210/0076* (2013.01); *A61F 2220/0058* (2013.01); *A61F 2230/005* (2013.01); *A61F 2230/008* (2013.01); *A61F 2230/0054* (2013.01); *A61F 2230/0067* (2013.01); *A61F 2230/0069* (2013.01); *A61F 2250/0039* (2013.01)

(58) Field of Classification Search
CPC ...... A61F 2230/0067; A61F 2230/0069; A61F 2250/0007; A61F 2250/0065
See application file for complete search history.

(56) References Cited

U.S. PATENT DOCUMENTS

| | | | |
|---|---|---|---|
| 8,092,523 | B2 | 1/2012 | Li et al. |
| 8,449,599 | B2 | 5/2013 | Chau et al. |
| 2005/0137682 | A1 | 6/2005 | Justino |
| 2005/0137690 | A1 | 6/2005 | Salahieh et al. |
| 2006/0058872 | A1* | 3/2006 | Salahieh ............... A61F 2/2439 623/2.18 |
| 2006/0287717 | A1* | 12/2006 | Rowe ................... A61F 2/2445 623/2.11 |
| 2008/0147179 | A1 | 6/2008 | Cai et al. |
| 2008/0183273 | A1 | 7/2008 | Mesana et al. |
| 2008/0275540 | A1* | 11/2008 | Wen ..................... A61F 2/2418 623/1.26 |
| 2008/0300678 | A1* | 12/2008 | Eidenschink ......... A61F 2/2436 623/2.18 |
| 2009/0210047 | A1 | 8/2009 | Amplatz et al. |
| 2010/0023046 | A1 | 1/2010 | Heidner et al. |
| 2010/0168839 | A1* | 7/2010 | Braido ................... A61L 27/54 623/1.26 |
| 2010/0204781 | A1 | 8/2010 | Alkhatib |
| 2011/0218619 | A1 | 9/2011 | Benichou et al. |
| 2013/0204360 | A1 | 8/2013 | Gainor |
| 2014/0128968 | A1 | 5/2014 | Benichou et al. |
| 2021/0196455 | A1* | 7/2021 | Morriss ................ A61F 2/2445 |

FOREIGN PATENT DOCUMENTS

| | | |
|---|---|---|
| WO | 2008097589 A1 | 8/2008 |
| WO | 2010098857 A1 | 9/2010 |

* cited by examiner

MULTI-LAYER STENT

CROSS-REFERENCE TO RELATED APPLICATIONS

This application is a continuation of U.S. patent application Ser. No. 15/365,040 filed Nov. 30, 2016, now abandoned, which is a continuation of U.S. patent application Ser. No. 14/124,092 filed Mar. 28, 2014, now U.S. Pat. No. 9,532,887, which is a national phase entry under 35 U.S.C. § 371 of International Application No. PCT/US2012/042059, filed Jun. 12, 2012, published in English, which claims the benefit of the filing date of U.S. Provisional Patent Application No. 61/497,291, filed Jun. 15, 2011, the disclosures of which are hereby incorporated by reference herein.

The present disclosure relates to collapsible prosthetic heart valves and, more specifically, to prosthetic heart valves having two or more stent layers.

A healthy aortic valve acts as a one-way valve, opening to allow blood to flow out of the left ventricle of the heart, and then closing to prevent blood from flowing back into the heart. Diseased or damaged aortic valves may not close properly and thus allow blood to flow back into the heart. Damage to aortic valves may occur due to congenital defects, the natural aging process, infection or scarring. Diseased or damaged aortic valves sometimes need to be replaced to prevent heart failure. In such cases, collapsible prosthetic heart valves may be used to replace the native aortic valve.

Current collapsible prosthetic heart valve designs may be used in high-risk patients who may need a cardiac valve replacement, but who are not appropriate candidates for conventional open-chest, open-heart surgery. These collapsible and re-expandable prosthetic heart valves can be implanted transapically or percutaneously through the arterial system. One percutaneous delivery method entails introducing a collapsible prosthetic heart valve through a patient's femoral artery. This delivery method is referred to as a transfemoral approach.

The stent frame of a conventional collapsible prosthetic heart valve may have a diamond or serpentine pattern defining an acute angle θ at the longitudinal ends of each cell, as shown in FIG. 1. These stent frames are difficult to reposition during placement due to the high forces required to slide a delivery sheath back over a partially deployed and expanded stent.

The stent frame may alternatively be constructed with cells defining substantially equal angles at all corners or obtuse angles at the longitudinal ends of each cell, as shown in FIG. 2. This kind of stent frame design also has its shortcomings. For example, the large amount of elongation that occurs when this kind of stent frame is crimped may cause the cuff and the leaflet material to fail.

There therefore exists a need for an improved stent design which can be easily compressed by the delivery sheath during placement in order to facilitate repositioning, but which does not hasten cuff and leaflet failure during compression and expansion.

BRIEF SUMMARY OF THE INVENTION

The present invention addresses this need.

According to one embodiment of the present invention, a collapsible prosthetic heart valve includes a stent including a foldable section, an annulus section, and an aortic section arranged in series, the stent being movable between an unfolded condition in which the foldable section is spaced from the annulus section in a longitudinal direction, and a folded condition in which the foldable section is at least partially positioned within the annulus section; and a valve assembly attached to the foldable section of the stent. In embodiments hereof, the foldable section, the annulus section and the aortic section may be formed integrally with one another. In further embodiments hereof, the valve assembly may include a cuff and a plurality of leaflets, and at least a portion of the cuff may be attached inside the annulus section.

The stent may have a collapsed condition and an expanded condition, the annulus section lengthening in the longitudinal direction by a first elongation percentage upon movement from the expanded condition to the collapsed condition and the foldable section lengthening in the longitudinal direction by a second elongation percentage upon movement from the expanded condition to the collapsed condition, the first elongation percentage being greater than the second elongation percentage.

The annulus section may include a plurality of cells and the foldable section may include a plurality of cells, each cell having a substantially diamond shape with four corners when the stent is in the expanded condition. Each cell in the annulus section may include two corners substantially aligned with one another in the longitudinal direction, and each cell in the foldable section may include two corners substantially aligned with one another in the longitudinal direction. The two corners in the annulus section may define a larger angle than the two corners in the foldable section. The two corners in the annulus section may each define an obtuse angle, and the two corners in the foldable section may each define an acute angle.

Another embodiment of the present invention provides a collapsible prosthetic heart valve, including a stent that includes a clamping section, a foldable section, and an annulus section arranged in series, the stent being movable between an unfolded condition in which the foldable section is spaced from the annulus section in a longitudinal direction, and a folded condition in which the foldable section is inverted and folded over at least a portion of the annulus section; and a valve assembly attached to the stent and at least partially disposed inside the annulus section of the stent. The valve assembly may include a cuff and a plurality of leaflets.

The clamping section may be spaced from the foldable section in the longitudinal direction when the stent is in the unfolded condition. Moreover, the clamping section may be folded outward of at least a portion of the foldable section when the stent is in the folded condition.

The stent may have a collapsed condition and an expanded condition, and the annulus section, the foldable section and the clamping section may each include a plurality of cells, each cell having a substantially diamond shape with four corners when the stent is in the expanded condition.

Yet another embodiment of the present invention provides a collapsible prosthetic heart valve, including a stent that includes a foldable section and an annulus section arranged in series, the stent being movable between an unfolded condition in which the foldable section is spaced from the annulus section in a longitudinal direction, and a folded condition in which at least a portion of the foldable section is inverted and folded over at least a portion of the annulus section; and a valve assembly attached inside the annulus section of the stent.

The foldable section may include a first region and a second region, the first and second regions being divided by a folding line. The first region may be inverted and folded over at least a portion of the annulus section when the stent is in the folded condition. The second region may be folded outward of at least a portion of the first region when the stent is in the folded condition.

BRIEF DESCRIPTION OF THE DRAWINGS

Various embodiments of the present invention will now be described with reference to the appended drawings. It is to be appreciated that these drawings depict only some embodiments of the invention and therefore are not to be considered limiting of its scope.

FIG. 6b is a perspective view from one end of the multi-layer stent of FIG. 6a;

FIG. 6c is a perspective view from the opposite end of the multi-layer stent of FIG. 6a;

DETAILED DESCRIPTION

As used herein, the term "proximal," when used in connection with a prosthetic heart valve, refers to the end of the prosthetic heart valve closest to the heart when the heart valve is implanted in a patient, whereas the term "distal," when used in connection with a prosthetic heart valve, refers to the end of the prosthetic heart valve farthest from the heart when the prosthetic heart valve is implanted in a patient.

Figure 1:
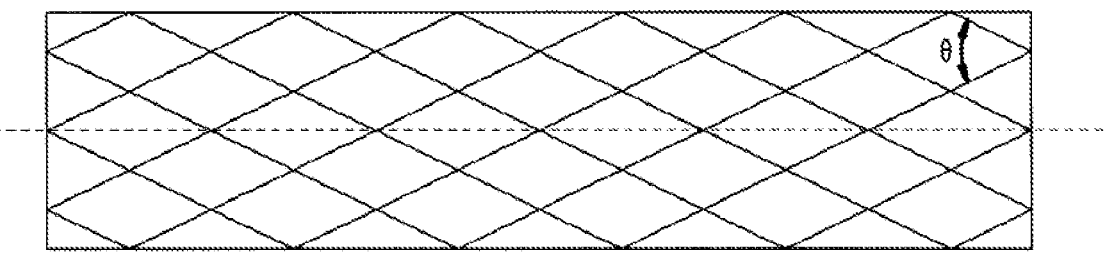
FIG. 1 is a side view of a conventional stent frame with cells defining acute angles at their longitudinal ends.
Figure 2:
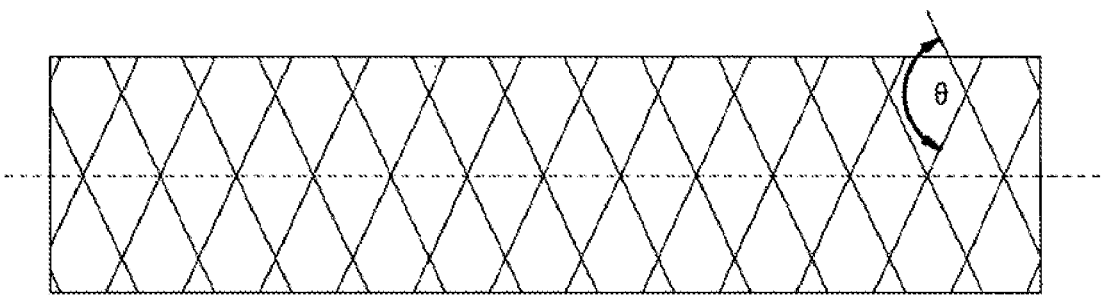
FIG. 2 is a side view of a stent frame with cells defining obtuse angles at their longitudinal ends.
Figure 3:
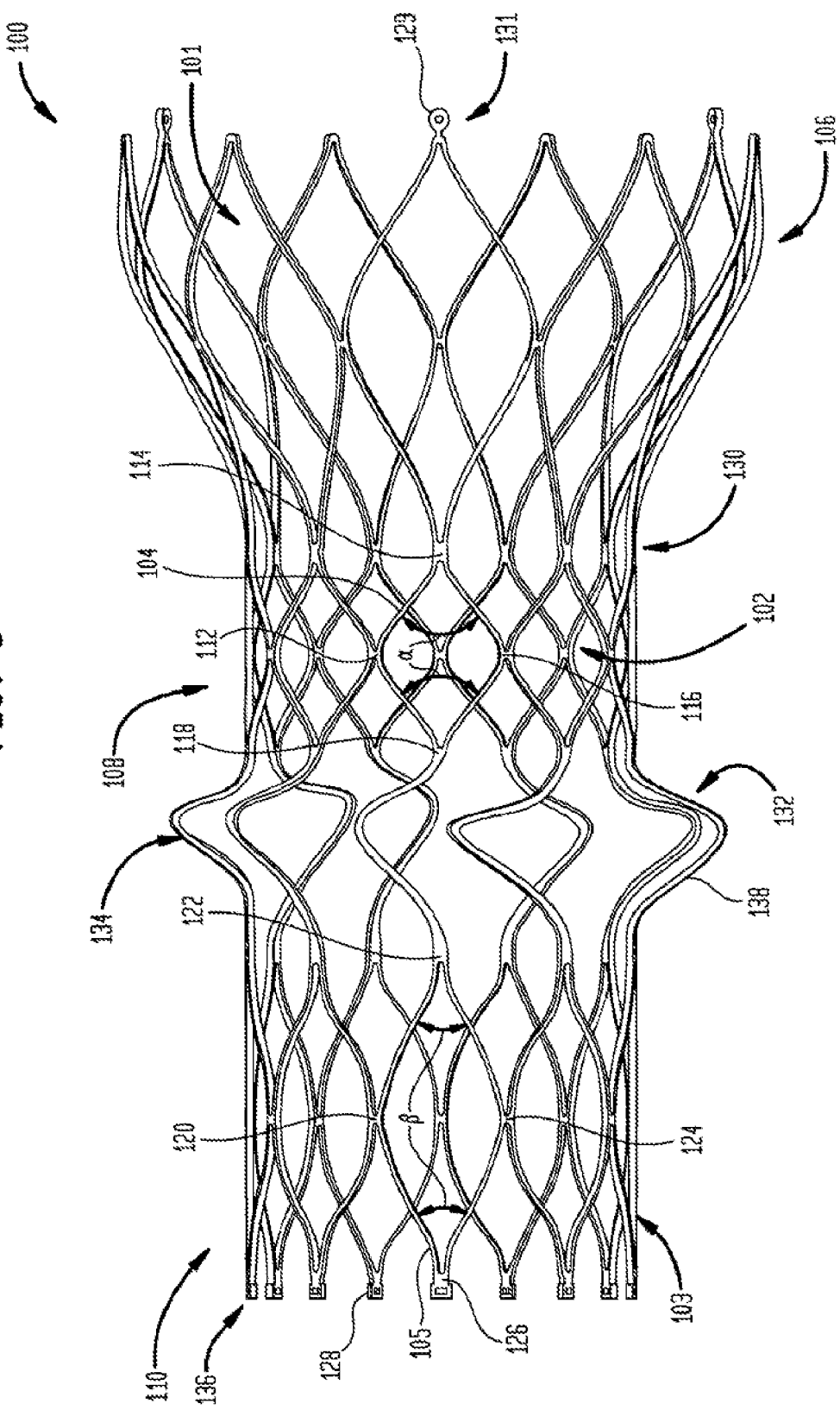
FIG. 3 is a side perspective view of a multi-layer stent according to one embodiment of the present invention in an unfolded condition.
Figure 4:
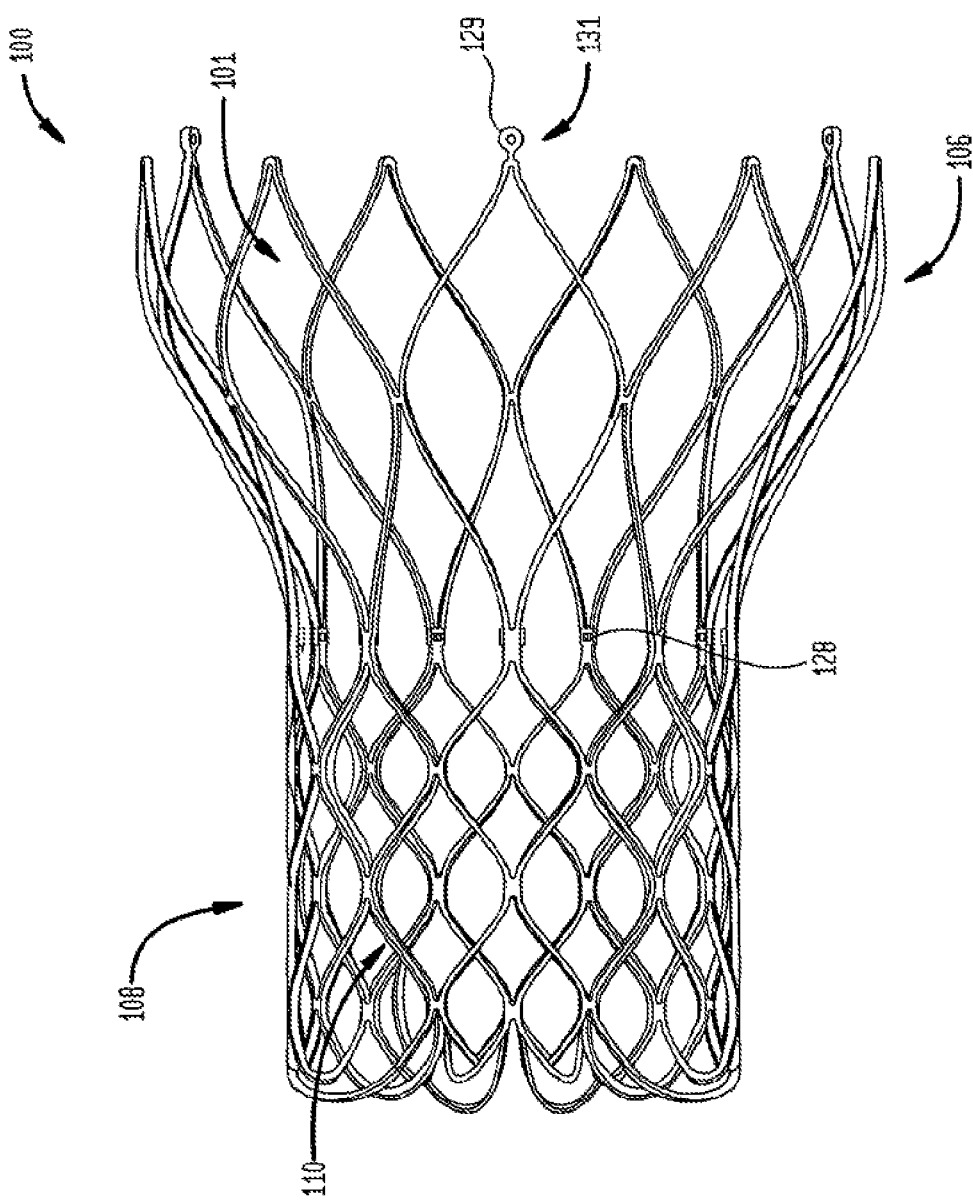
FIG. 4 is a side perspective view of the multi-layer stent of FIG. 3 in a folded condition.
Figure 5:
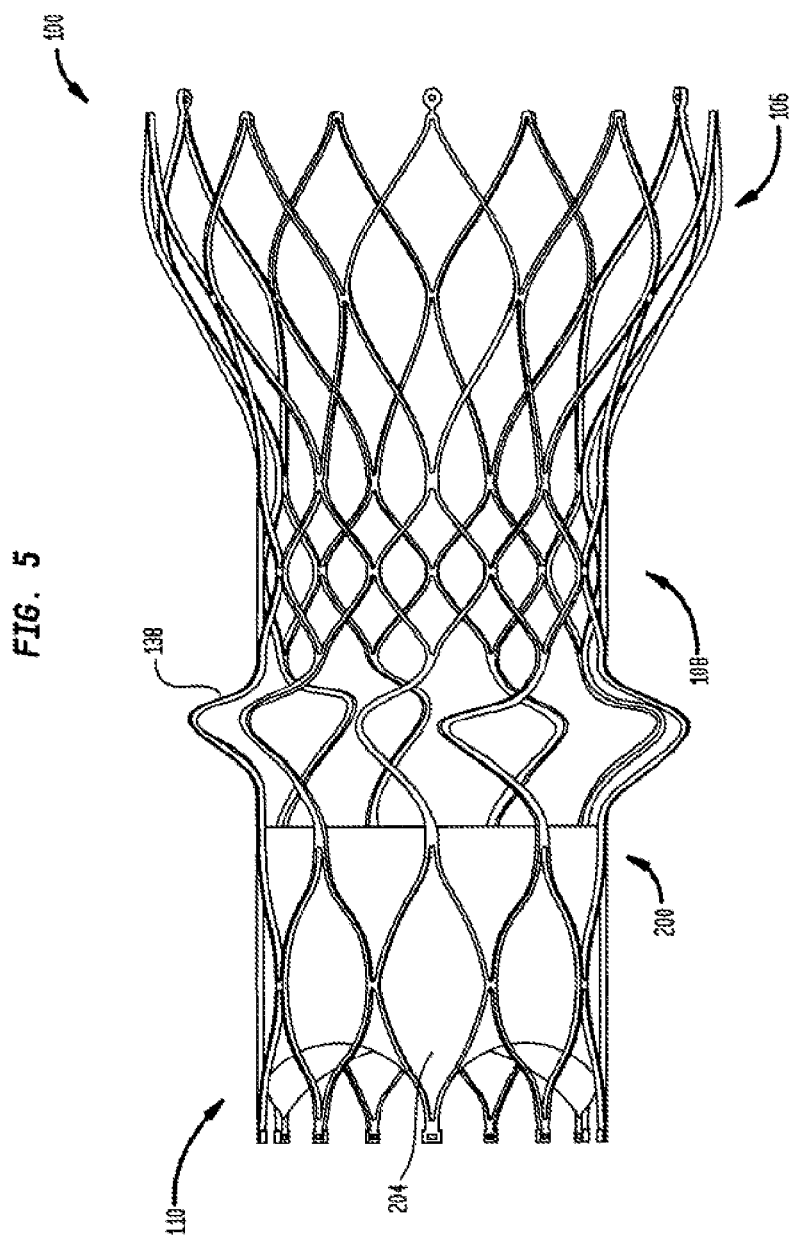
FIG. 5 is a side perspective view of the multi-layer stent of FIG. 3 in an unfolded condition with a valve assembly attached thereto.

FIGS. 3 and 4 illustrate a collapsible multi-layer stent or frame 100, which is part of a collapsible prosthetic heart valve. As discussed in detail below, the collapsible prosthetic heart valve also includes a valve assembly 200 supported by the stent 100, as seen in FIG. 5. The stent 100 may be wholly or partly made of any biocompatible material suitable for allowing the stent to expand and collapse. Suitable biocompatible materials include, but are not limited to, metals or metal alloys, such as nitinol, synthetic polymers, or biopolymers capable of functioning as a stent.

The stent 100 includes at least an aortic section 106 at one end, an annulus section 108 in the middle, and a foldable section 110 at the other end. Each of the aortic section 106, annulus section 108, and foldable section 110 includes a plurality of cells. More particularly, aortic section 106 includes a plurality of cells 101; annulus section 108 includes a plurality of cells 102; and foldable section 110 includes a plurality of cells 103. The stent 100 may be cut in one piece from a tube, such as by laser cutting. Alternatively, the stent 100 may be formed of several discrete pieces connected together. For example, the aortic section 106 and annulus section 108 may be formed together in one piece, while foldable section 110 may be formed as a separate piece and subsequently connected to the annulus section 108. In such embodiment, foldable section 110 may be attached to the annulus section 108 by sutures, wires, welding or any other suitable attachment method or means. The point of attachment of the foldable section 110 to the annulus section 108 may be located at the first end 130 of the annulus section or at the second end 132 of the annulus section. Alternatively, the foldable section 110 may be attached to the annulus section 108 by a sliding connection coupled to both the first end 130 and the second end 132 of the annulus section.

The cells 101 of aortic section 106 may be arranged in one or more annular rows extending around the circumference of the aortic section. When stent 100 is in the expanded condition, the cells 101 of aortic section 106 may have substantially a diamond shape. As seen in FIG. 3, when stent 100 is in the expanded condition, the aortic section 106 may have a circumference or diameter which increases in size from the end of the aortic section connected to the annulus section 108 to the free end of the aortic section. The aortic section 106 may include retaining members 129, such as eyelets, at its free end 131. The retaining members 129 are intended to engage in corresponding recesses in the delivery device to hold stent 100 in a fixed and controllable position during delivery and placement of the stent in a patient.

In the expanded condition of stent 100, the annulus section 108 may have a substantially uniform circumference or diameter along its length from first end 130 to second end 132. Each of the cells 102 of the annulus section 108 may be formed by four struts 104 which together define substantially diamond shaped cells when stent 100 is in the expanded condition. The struts 104 of each cell 102 are connected to one another in end to end fashion, with the connections each occurring at a cell corner. Each cell 102 has four cell corners 112, 114, 116, and 118. Corners 112 and 116 of a cell 102 are substantially aligned in the circumferential direction of the stent 100, while corners 114 and 118 of the cell are substantially aligned in the axial direction of the stent.

The angle α formed between adjacent struts 104 at corners 114 and 118 of each cell 102 may be substantially identical throughout the entirety of the annulus section 108. The angle α may be equal to or greater than about 90°. Preferably, angle α may be about 110°. The angle α at the longitudinal ends of the cells 102 affects the elongation of the annulus section 108 when subjected to compressive forces by a delivery system. The elongation of the annulus section is directly proportional to the angle α at the cell corners 114 and 118. Thus, increasing the expanded angle α will cause an increase in the elongation of the annulus section 108 when the stent is compressed. Annulus section 108 preferably will exhibit a percent elongation from the expanded condition to the compressed condition of between about 30% and about 50%, with an elongation of about 50% being preferred.

The foldable section 110 is connected at its first end 134 to the annulus section 108 and may also include enlarged eyelets 128 at its free end 136. The eyelets 128 may be used for suturing the commissures of the prosthetic valve assembly to the stent 100, thereby attaching the prosthetic valve assembly to the stent. In addition, the eyelets 128 may be used for suturing the foldable section 110 to the first end 130 of the annulus section 108 when the foldable section is in the folded condition to prevent excessive flexing of the foldable section. Excessive flexing of the foldable section 110 should be avoided as it could cause fatigue fractures.

As noted previously, the foldable section 110 includes a plurality of cells 103, which may be arranged in one or more annular rows extending around the circumference of the foldable section 110. Each cell 103 of the foldable section 110 may be formed by four struts 105, which together define a substantially diamond shape when stent 100 is in the expanded condition. The struts 105 of each cell 103 are connected to one another in end to end fashion, with each connection occurring at a cell corner. Each cell 103 has four cell corners 120, 122, 124, and 126. Corners 120 and 124 are substantially aligned in the circumferential direction of the stent, while corners 122 and 126 of each cell 103 are substantially aligned in the axial direction of the stent.

The angle β formed between adjacent struts 105 at corners 122 and 126 of each cell 103 is preferably smaller than angle α, and may be acute. The angle β may range from about 50° to about 70°, and preferably is about 60°. The angle β at the longitudinal ends of the cells 103 affects the elongation of the foldable section 110 when subjected to compressive forces by a delivery system. The elongation of the foldable section 110 is directly proportional to the angle β at the cell corners 122 and 126. Therefore, decreasing the expanded angle β will cause a decrease in the elongation of the foldable section 110 when it is compressed.

As a result of its larger cell angles α, the annulus section 108 has a higher percent elongation than the foldable section 110. For instance, the annulus section 108 may have a percent elongation ranging from about 30% to about 50%, while foldable section 110 may have a percent elongation ranging from about 7% to about 10%. An elongation of about 10% for the foldable section 110 is highly preferred.

The valve assembly 200 should not be attached to a section of the stent 100 having a high elongation since the large stent distortion during compression may cause the valve assembly to tear or become detached from the stent. Rather, the valve assembly 200 should be attached to a section of the stent having a lower elongation during compression to prevent the valve assembly from being damaged. Accordingly, the valve assembly 200 preferably is attached to the foldable section 110 which exhibits a significantly lower elongation during its compression than annulus section 108.

The foldable section 110 may be inverted or folded under the annulus section 108 before use, as seen in FIG. 4. To this end, foldable section 110 includes a plurality of bendable struts 138 at its first end 134. The bendable struts 138 couple foldable section 110 to annulus section 108 and allow the foldable section to be inverted under the annulus section.

Figure 6A:
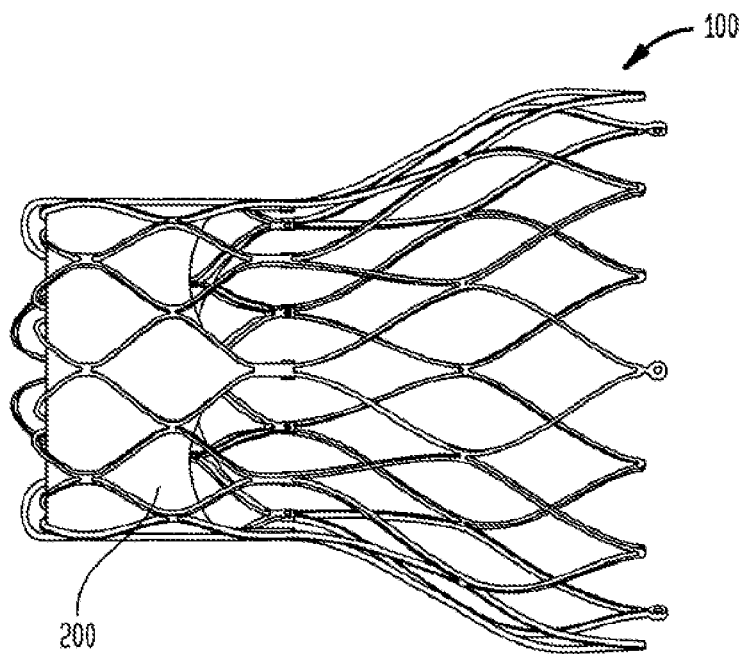
FIG. 6a is a side perspective view of the multi-layer stent of FIG. 5 in a folded condition with the valve assembly attached thereto.

As seen in FIGS. 5, 6a, 6b and 6c, a valve assembly 200 may be attached to the interior of foldable section 110 of stent 100. The valve assembly 200 includes a plurality of leaflets 202, which collectively function as a one-way valve, and which may be wholly or partly formed of tissue or any suitable polymer. Suitable valve assemblies are described in U.S. Pat. No. 8,092,523 and U.S. Patent Application Publication No. 2008/0147179, filed Dec. 19, 2007, the entire disclosures of which are hereby incorporated by reference. The valve assembly 200 may also include a cuff 204 disposed in an interior and/or exterior portion of foldable section 110 adjacent the leaflets 202. The cuff 204 may be foldable along with foldable section 110, as seen in FIG. 6a. At least a portion of the cuff 204 may be attached to bendable struts 138, to the annulus section 108 of stent 100, and/or to the interior and/or exterior (in the unfolded condition) of the foldable section 110.

FIG. 5 shows the valve assembly 200 attached to the interior of the foldable section 110 of stent 100 in the unfolded condition. The valve assembly 200 is attached to the foldable section 110 of stent 100 so that, when the foldable section is inverted under annulus section 108, as illustrated in FIG. 6a, the leaflets 202 of the valve assembly permit blood to flow from the annulus section to the aortic section 106 of the stent, while preventing blood from flowing from the aortic section to the annulus section. Rather than being attached to the interior of foldable section 110 of the stent 100, the valve assembly 200 may be attached to the interior of the annulus section 108 of the stent. For reasons discussed above regarding potential damage to the valve assembly 200 on compression of the stent, however, attachment to annulus section 108 is less preferred.

Figure 6B:
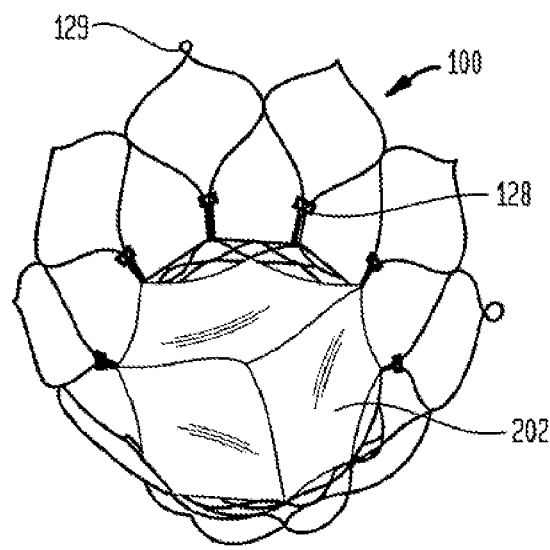
Figure 6C:
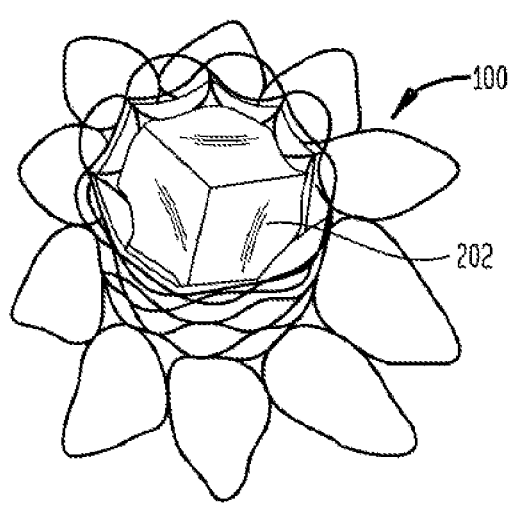

During operation, the collapsible prosthetic heart valve, including stent 100 and valve assembly 200, may be implanted in a native valve annulus of a patient with the foldable section 110 in the folded condition, as shown in FIGS. 6a, 6b, and 6c. The foldable section 110 of stent 100 may be inverted to its folded condition during assembly or during deployment. When foldable section 110 is in the folded condition, it is at least partially positioned within the annulus section 108 of the stent 100. At this point, the valve assembly 200 is attached to the foldable section 110, which has a low elongation during compression of stent 100. Due to the low elongation of foldable section 110, the valve assembly 200 is less likely to be damaged during initial compression of stent 100 or during a resheathing procedure, should that become necessary. On the other hand, the annulus section 108 has a larger elongation during compression of stent 100, but requires small forces to be radially compressed, thereby facilitating resheathing. The size of angles α formed between adjacent struts 104 at the corners 114 and 118 of each cell 102 allows the force applied in the axial direction to stent 100 as a delivery sheath is slid thereover to be more effectively translated to radial compression. The size of cell corner angles α in the annulus section 108 also allows the same force to be achieved with thinner struts because the force components are directed more along the length of the strut. As a consequence, the entire collapsible prosthetic heart valve can be pulled safely into the delivery sheath via the annulus section 108 of stent 100.

Figure 7A:
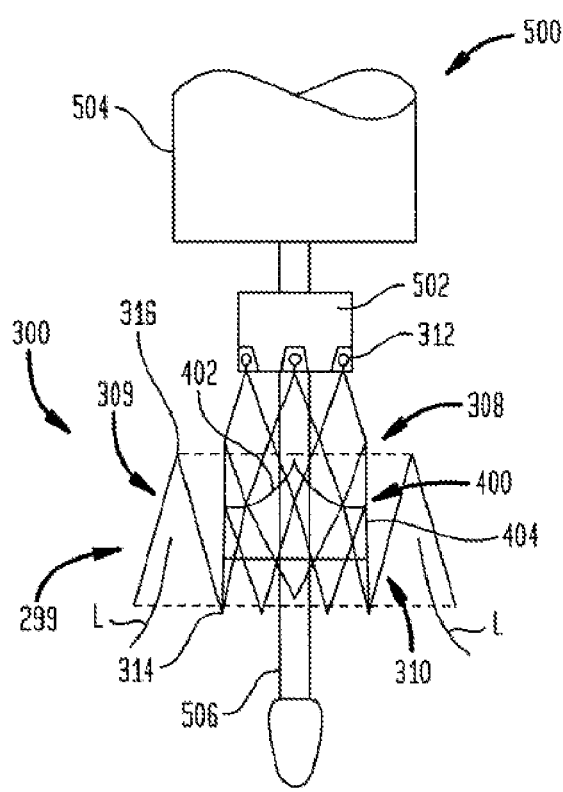
FIG. 7a is a highly schematic side view of another embodiment of a multi-layer stent of the present invention in an expanded and folded condition and coupled to a delivery system.
Figure 7B:
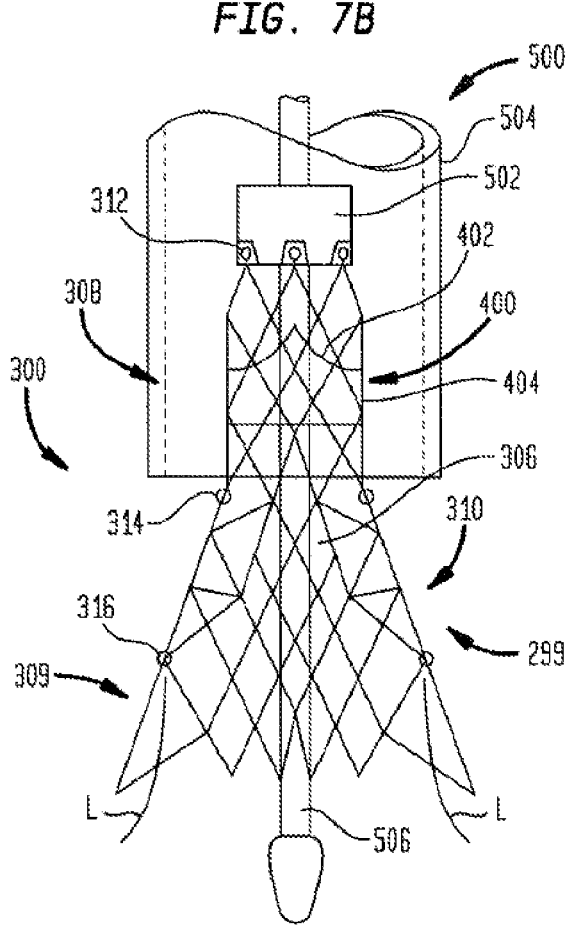
FIG. 7b is a highly schematic side view of the multi-layer stent of FIG. 7a in an expanded and unfolded condition.
Figure 7C:
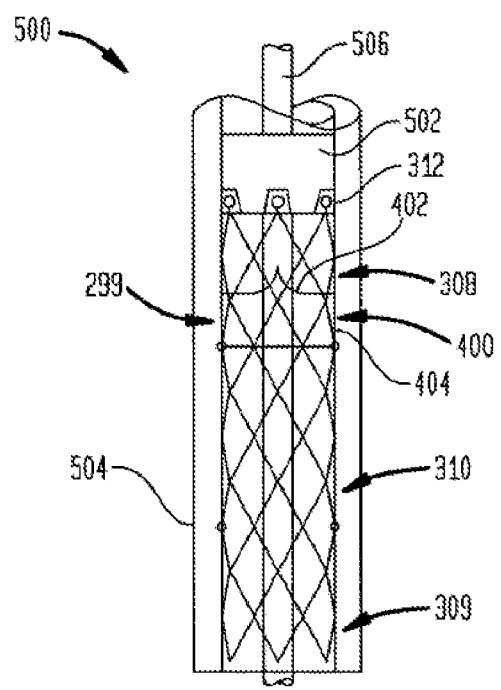
FIG. 7c is a highly schematic side view of the multi-layer stent of FIG. 7a in a collapsed and unfolded condition inside a delivery catheter.

FIGS. 7a, 7b, and 7c illustrate another embodiment of a collapsible heart valve 299 and a method of implanting the same near a native valve annulus. This collapsible prosthetic heart valve 299 includes a stent or frame 300 and a valve assembly 400. The stent 300 is made entirely or partly of a suitable shape memory material having an unstressed state and a deformed state. Suitable shape memory materials include biocompatible shape memory metals or alloys, such as nitinol, and biocompatible shape memory polymers.

The stent 300 has an expanded and unfolded condition, as seen in FIG. 7b, an expanded and folded condition, such as seen in FIG. 7a, and a collapsed and unfolded condition, as seen in FIG. 7c. The stent 300 includes an annulus section 308, a clamping section 309, and a foldable or invertible section 310. Each of the annulus section 308, clamping section 309, and foldable or invertible section 310 includes a plurality of cells 306 extending around its periphery. Since heart valve 299 captures at least a portion of the native valve leaflets between the clamping section 309 and the foldable section 310 on deployment, as will be described further below, thereby holding the heart valve in place in the native valve annulus, stent 300 need not be formed with an aortic section.

The annulus section 308 of the stent 300 is located at one end of the stent and may have a substantially cylindrical shape when the stent is in the expanded condition, as seen in FIG. 7b. One or more retaining members 312, such as eyelets, may be provided at the free end of the annulus section 308 for connecting the stent 300 to a delivery system 500 during delivery and placement of the stent in a patient. The foldable section 310 of the stent 300 may be connected to the annulus section 308 and may have a substantially frusto-conical shape when the stent is in the expanded condition, as seen in FIG. 7b. When the stent 300 is in the collapsed condition, on the other hand, the foldable section 310 may have a substantially cylindrical shape, as seen in FIG. 7c. The foldable section 310 includes a first bendable portion 314 near its connection to annulus section 308. The foldable section 310 may be inverted at the first bendable portion 314 and folded over at least a portion of the annulus section 308.

The clamping section 309 of the stent 300 may be connected to the foldable section 310 at the other end of stent 300 and may also have a substantially frusto-conical shape when the stent is in an expanded condition, as seen in FIG. 7b, and a substantially cylindrical shape when the stent is in the collapsed condition, as seen in FIG. 7c. A second bendable portion 316 near the connection of foldable section 310 to clamping section 309 enables the clamping section to be inverted and folded in the opposite direction back over the foldable section, as seen in FIG. 7a.

A valve assembly 400 may be attached to the inner surface of the annulus section 308 and may include a cuff 404 and a plurality of leaflets 402 attached to the cuff and/or to stent 300. The leaflets 402 collectively function as a one-way valve. The valve assembly 400 may be entirely or partly made of tissue or any suitable polymer.

The prosthetic heart valve 299 depicted in FIGS. 7a-7c may be implanted in a native valve annulus of a patient using any suitable delivery system, such as delivery system 500. Delivery system 500 includes a support shaft 506 around which the collapsed valve may be mounted, and a distal sheath 504 slidable relative to the support shaft to selectively cover and uncover the valve. A retaining element 502 mounted on the support shaft 506 may include recesses to securely receive the retaining members 312 of the stent 300.

The delivery system 500 may be used to implant the collapsible prosthetic heart valve 299 transfemorally or transapically. Other delivery methods are also envisioned, including the use of a trans-subclavian approach. Before inserting the prosthetic heart valve 299 into the patient, the heart valve should be mounted around the support shaft 506 of the delivery system 500 in the collapsed and unfolded condition, as seen in FIG. 7c, with retaining members 312 positioned in the recesses of the retaining element 502. Subsequently, the distal sheath 504 should be slid over the valve to hold it in the collapsed condition for delivery. The delivery system 500 may then be inserted into the patient until the distal sheath 504 reaches the desired site (e.g., the native valve annulus). Once at the desired site, the user may slide the distal sheath 504 relative to the support shaft 506 to uncover a portion of the stent 300, as seen in FIG. 7b, to initiate deployment of heart valve 299. If the heart valve 299 is being deployed in the correct position, the user may expose the entire stent 300 to complete the deployment process. Otherwise, the user may slide the distal sheath 504 in the opposite direction to again cover the stent 300 and reposition the delivery system 500 to the correct position.

When the heart valve 299 has been completely deployed, the stent 300 automatically converts from the unfolded shape (i.e., stressed state), as seen in FIG. 7b, to the folded shape (i.e., unstressed state), as seen in FIG. 7a. During this conversion, the first bendable portion 314 of the foldable section 310 bends to invert the foldable section over at least a portion of annulus section 308. The second bendable portion 316 of the foldable section 310 also bends, but in the opposite direction, to fold the clamping section 309 back over at least a portion of the foldable section 310. Thus, in the folded condition of stent 300, the clamping section 309 is positioned radially outward of the foldable section 310 and the valve assembly 400. As the clamping section 309 folds back over the foldables section 310, it captures at least a portion of the native leaflets L and sandwiches them between the clamping section and the foldable section 310, as seen in FIG. 7a. This clamping of the folded stent 300 to the native valve leaflets L acts to secure heart valve 299 in the native valve annulus.

When the stent 300 is in the expanded and folded condition as seen in FIG. 7a, at least a portion of the cuff 404 of the valve assembly 400 may extend beyond the first bendable portion 314 and may contact the native leaflets L to help prevent regurgitation of blood between the native leaflets and the outer portion of the valve assembly. That is, the contact between the cuff 404 and the native leaflets helps to prevent paravalvular leaks.

While the foregoing describes the deployment of prosthetic heart valve 299 in the native annulus of a patient to replace the patient's native valve, in certain circumstances, prosthetic heart valve 299 (as well as the other prosthetic heart valves described herein) may be deployed within a previously implanted prosthetic heart valve that is no longer performing optimally. In that situation, the prosthetic heart valve 299 may be deployed in the manner described above. However, rather than having a portion of native valve leaflets L captured as clamping section 309 folds back over at least a portion of foldable section 310, the clamping section may capture the prosthetic leaflets or stent frame of the previously implanted prosthetic heart valve in order to hold the newly inserted heart valve in its implanted position.

Figure 8A:
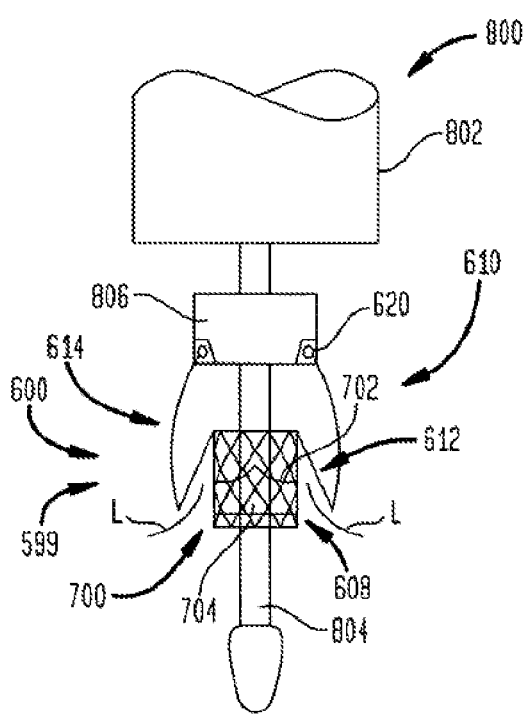
FIG. 8a is a highly schematic side view of another embodiment of a multi-layer stent of the present invention in an expanded and folded condition.
Figure 8B:
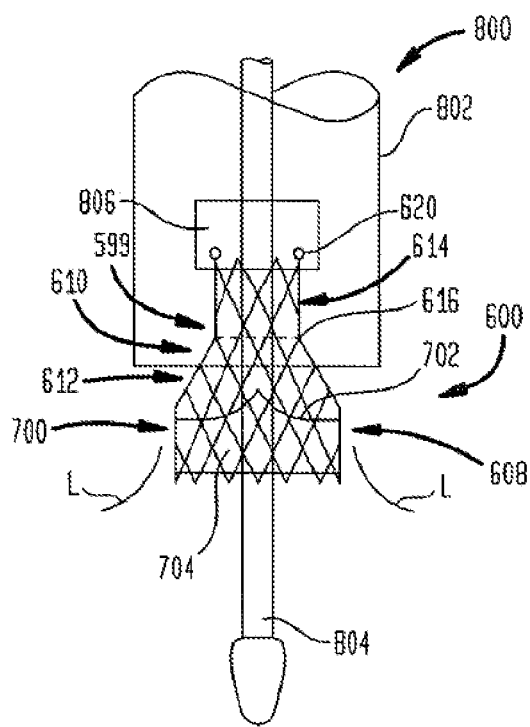
FIG. 8b is a highly schematic side view of the multi-layer stent of FIG. 8a in an expanded and unfolded condition.
Figure 8C:
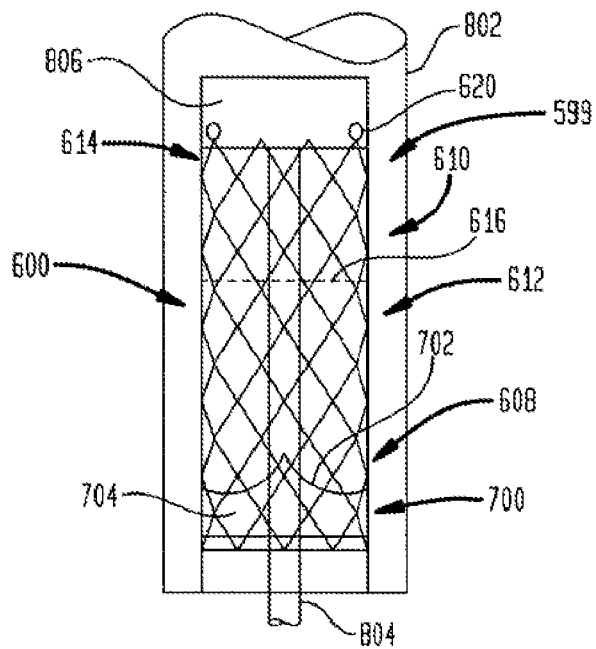
FIG. 8c is a highly schematic side view of the multi-layer stent of FIG. 8a in a collapsed condition inside a delivery catheter.

FIGS. 8a-8c show a collapsible prosthetic heart valve 599 according to yet another embodiment of the present invention. This heart valve includes an expandable/collapsible stent or frame 600 made partly or entirely of a shape memory material. The stent 600 includes an annulus section 608 and a foldable section 610 and, as with heart valve 299 described above, may eliminate an aortic section. Each of the annulus section 608 and the foldable section 610 includes a plurality of cells extending around its periphery, enabling stent 600 to move between an expanded condition and a collapsed condition. When the stent 600 is in the collapsed condition, the annulus section 608 and the foldable section 610 may each have a substantially cylindrical shape, as shown in FIG. 8c.

The foldable section 610 has a first region 612 adjacent annulus section 608 and a second region 614 spaced from the annulus section, with the two regions being divided by a folding line 616. As a result, the foldable section 610 can bend along the folding line 616 between an unstressed folded condition, as seen in FIG. 8a, and a deformed condition, as seen in FIG. 8c, in which the foldable section 610 is unfolded. In the deformed condition, in which the foldable section 610 is stressed, stent 600 has a substantially cylindrical configuration, with the first region 612 of the foldable section positioned between the second region 614 thereof and the annulus section 608. In the unstressed folded condition, the first region 612 of the foldable section 610 may be inverted and folded over at least a portion of the annulus section 608 of the stent 600, and the second region 614 of the foldable section may be inverted and folded in the opposite direction back over at least a portion of the first region 612. The second region 614 of foldable section 610 may include one or more retaining members 620, such as eyelets, for facilitating a secure attachment between stent 600 and a delivery system 800.

A valve assembly 700 may be attached to the inner surface of the annulus section 608 and may include a cuff 704 and a plurality of leaflets 702 attached to the cuff and/or to stent 600. The leaflets 702 collectively function as a one-way valve. The valve assembly 700 may be entirely or partially made of a suitable polymer or tissue.

The prosthetic heart valve depicted in FIGS. 8a-8c may be implanted in a native valve annulus of a patient using a transfemoral approach, a transapical approach, a trans-subclavian approach, and by other known methods using any suitable delivery system, including the delivery system 800. The delivery system 800 includes a support shaft 804 around which the collapsed valve may be mounted, and a distal sheath 802 slidable relative to the support shaft to selectively cover and uncover the valve. A retaining element 806 mounted on the support shaft 804 includes recesses adapted to receive the retaining members 620 of the stent 600 for attaching the stent to the delivery system 800.

Before inserting the prosthetic heart valve 599 depicted in FIGS. 8a-8c into the patient, the heart valve should be mounted around the support shaft 804 of the delivery system 800 in the collapsed and unfolded condition, as shown in FIG. 8c, with the retaining members 620 positioned in the recesses of the retaining element 806. The distal sheath 802 should then be slid over the valve to hold the valve in the collapsed condition for delivery. The delivery system 800 may then be inserted into the patient until the distal sheath 802 reaches the desired site (e.g., the native valve annulus). During insertion, the distal sheath 802 maintains the stent 600 in the deformed (i.e., unfolded) state, as seen in FIG. 8c. The distal sheath 802 may then be slid relative to the support shaft 804 to uncover at least a portion of the stent 600 for deployment of heart valve 599. The user may then determine if the heart valve 599 is being deployed at the correct position. If a correction is necessary, the user may slide the distal sheath 802 in the opposite direction to again cover the stent 600, and may reposition the delivery system 800 at the proper location. Once the delivery system 800 is at the correct location, the user may again slide the distal sheath 802 to uncover the stent 600 and deploy the heart valve. Upon complete deployment of heart valve 599, the stent 600 automatically converts from its deformed condition (i.e., stressed state), as shown in FIG. 8c, to its folded condition (i.e., unstressed state), as shown in FIG. 8a. During this conversion, the first region 612 of the foldable section 610 inverts and folds over at least a portion of the annulus section 608. This action causes the first region 612 to deflect toward the native leaflets L and to urge the leaflets toward the annulus section 608 of the stent, sandwiching them between the first region and the annulus section, as seen in FIG. 8a. The second region 614 of the stent 600 also inverts and folds in the opposite direction back over at least a portion of the first region 612. The clamping of the native leaflets L between the annulus section 608 and the first region 612 acts to secure heart valve 599 in the native valve annulus.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, any of the prosthetic heart valves described herein may be used to replace the mitral valve, tricuspid valve, aortic valve or pulmonic valve. In addition, the prosthetic heart valves described herein may be implanted within a previously implanted prosthetic valve.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic heart valve, comprising:
a stent extending in a longitudinal direction and including an outer stent section and an inner stent section, the outer stent section including a proximal end connected to the inner stent section, a free distal end, an annulus section adjacent the proximal end, and a plurality of diamond-shaped cells arranged in a first annular row, the inner stent section including a plurality of diamond-shaped cells arranged in a second annular row, the stent having an expanded use configuration and a collapsed configuration, the stent in the expanded use configuration having an annular shape around an axis extending in the longitudinal direction; and
a valve assembly coupled to the inner stent section,
wherein in the collapsed configuration the outer stent section does not overlap with the inner stent section and in the expanded use configuration at least a portion of the outer stent section is disposed radially outward of the inner stent section and overlaps with the inner stent section such that the diamond-shaped cells in the first annular row at least partially overlap with the diamond-shaped cells in the second annular row, the annulus section overlaps with the valve assembly, and the free distal end of the outer stent section does not overlap with the inner stent section.

2. The prosthetic heart valve as claimed in claim 1, wherein the outer stent section is formed integrally with the inner stent section.

3. The prosthetic heart valve as claimed in claim 1, wherein the outer stent section is formed separately from the inner stent section and is connected to the inner stent section.

4. The prosthetic heart valve as claimed in claim 1, wherein the valve assembly includes a cuff and a plurality of leaflets.

5. The prosthetic heart valve as claimed in claim 1, wherein the stent is movable between the collapsed configuration in which the inner stent section is spaced from the outer stent section in the longitudinal direction, and the expanded use configuration in which the outer stent section at least partially overlaps in directions radial to the longitudinal direction with the inner stent section.

6. The prosthetic heart valve as claimed in claim 5, wherein at least a portion of the stent inverts upon moving from the collapsed configuration to the expanded use configuration.

7. The prosthetic heart valve as claimed in claim 1, wherein the inner stent section has a free end, the free end including a plurality of eyelets.

8. The prosthetic heart valve as claimed in claim 1, wherein the inner stent section has a cylindrical shape around the axis extending in the longitudinal direction in the expanded use configuration.

9. The prosthetic heart valve as claimed in claim 1, wherein the inner stent section has a free end, the outer stent section overlapping in directions radial to the longitudinal direction with the free end of the inner stent section in the expanded use configuration.

10. An assembly, comprising:
a prosthetic heart valve including:
a stent extending in a longitudinal direction and including an outer stent section and an inner stent section, the stent having an expanded configuration and a collapsed configuration, the outer stent section including a first end connected to the inner stent section, a free second end, an annulus section and a plurality of diamond-shaped cells arranged in a first annular row, and the inner stent section including a plurality of diamond-shaped cells arranged in a second annular row; and
a valve assembly coupled to the inner stent section,
wherein in the collapsed configuration the outer stent section does not overlap with the inner stent section and in the expanded configuration the outer stent section is disposed radially outward of the inner stent section and at least partially overlaps with the inner stent section such that the diamond-shaped cells in the first annular row at least partially overlap with the diamond-shaped cells in the second annular row, the annulus section overlaps with the valve assembly, and the free second end of the outer stent section does not overlap with the inner stent section; and
a delivery device having a valve support for supporting the prosthetic heart valve and a sheath slidable relative to the valve support between a first position in which the sheath covers the prosthetic heart valve and maintains the prosthetic heart valve in the collapsed configuration, and a second position in which the sheath exposes the prosthetic heart valve for deployment, the inner stent section being connected to the outer stent section so that, upon deployment of the prosthetic heart valve from the delivery device, the outer stent section automatically folds relative to the inner stent section.

11. The assembly as claimed in claim 10, wherein, upon deployment of the prosthetic heart valve from the delivery device, the stent moves from the collapsed configuration in which the inner stent section is spaced from the outer stent section in the longitudinal direction, to the expanded configuration in which the outer stent section at least partially overlaps with the inner stent section.

12. The assembly as claimed in claim 11, wherein at least a portion of the stent inverts upon moving from the collapsed configuration to the expanded configuration.

13. The assembly as claimed in claim 10, wherein the inner stent section has a free end, the outer stent section overlapping with the free end of the inner stent section in the expanded configuration.

14. The prosthetic heart valve as claimed in claim 1, wherein the inner stent section is positioned within the annulus section of the outer stent section in the expanded use condition.

15. A prosthetic heart valve, comprising:
a stent extending in a longitudinal direction and including an outer stent section and an inner stent section, the outer stent section including a free first end, a second end connected to the inner stent section, and a plurality of diamond-shaped cells arranged in a first annular row, the inner stent section including a first end connected to the outer stent section, a free second end, an annulus section and a plurality of diamond-shaped cells arranged in a second annular row, the stent having an expanded use configuration and a collapsed configuration, the stent in the expanded use configuration having an annular shape around an axis extending in the longitudinal direction; and
a valve assembly coupled within the annulus section,
wherein in the collapsed configuration the outer stent section does not overlap with the inner stent section and in the expanded use configuration at least a portion of the outer stent section is disposed radially outward of the annulus section and overlaps with the valve assembly and with the inner stent section such that the diamond-shaped cells in the first annular row overlap with the diamond-shaped cells in the second annular row, the free first end of the outer stent section points in a first direction and the free second end of the inner stent section points in a direction opposite the first direction.

16. The prosthetic heart valve as claimed in claim 15, wherein at least a portion of the stent inverts upon moving from the collapsed configuration to the expanded use configuration.

17. The prosthetic heart valve as claimed in claim 15, wherein the outer stent section does not overlap in directions radial to the longitudinal direction with the free second end of the inner stent section in the expanded use configuration.

* * * * *